United States Patent
Sigmon, Jr. et al.

(10) Patent No.: US 11,490,790 B2
(45) Date of Patent: Nov. 8, 2022

(54) DEVICE FOR SHIELDING ENDOSCOPIC OPTICS WITH A FLUID BARRIER

(71) Applicant: COOK MEDICAL TECHNOLOGIES LLC, Bloomington, IN (US)

(72) Inventors: John Crowder Sigmon, Jr., Winston-Salem, NC (US); Gregory James Hardy, Colonie, NY (US); Shaun Davis Gittard, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 602 days.

(21) Appl. No.: 16/508,935

(22) Filed: Jul. 11, 2019

(65) Prior Publication Data

US 2020/0022565 A1    Jan. 23, 2020

Related U.S. Application Data (60) Provisional application No. 62/700,007, filed on Jul. 18, 2018.

(51) Int. Cl.
*A61B 1/00* (2006.01)
*A61B 1/018* (2006.01)
(Continued)

(52) U.S. Cl.
CPC ...... *A61B 1/00091* (2013.01); *A61B 1/00096* (2013.01); *A61B 1/018* (2013.01);
(Continued)

(58) Field of Classification Search
None
See application file for complete search history.

(56) References Cited

U.S. PATENT DOCUMENTS 4,175,545 A * 11/1979 Termanini ......... A61M 25/0069
600/479
4,582,067 A * 4/1986 Silverstein ............. A61B 8/445
600/455

(Continued)

FOREIGN PATENT DOCUMENTS

| JP | 2014-090847 A | 5/2014 |
| WO | WO 97/26034 A1 | 7/1997 |
| WO | WO 2016/110824 A1 | 7/2016 |

OTHER PUBLICATIONS

Nezhat, Ceana et al., "A Simple Solution to Lens Fogging during Robotic and Laparoscopic Surgery," JSLS, Published 2008, Citation p. 431.

(Continued)

*Primary Examiner* — Timothy J Neal
(74) *Attorney, Agent, or Firm* — Crowell & Moring LLP (57) ABSTRACT

The present embodiments provide systems and methods suitable for delivering an agent including a plurality of particles to a target site. In example embodiments, a system suitable for delivering an agent to a target site includes a catheter having a first wall defining a lumen sized for delivery of the agent to the target site. The catheter has a distal end terminating with a primary opening of the lumen, an opposing proximal end, and a longitudinal axis extending between the distal end and the proximal end. At least one secondary opening is formed at the distal end, wherein the secondary opening is configured to allow fluid to flow through the secondary opening to create a steady flow of fluid at an angle with respect to the longitudinal axis and prevent the plurality of particles from flowing through the secondary opening.

17 Claims, 3 Drawing Sheets

(51) Int. Cl.
    *A61B 1/12*    (2006.01)
    *A61M 25/00*   (2006.01)
    *A61M 25/06*   (2006.01)

(52) U.S. Cl.
    CPC .......... *A61B 1/126* (2013.01); *A61M 25/007* (2013.01); *A61M 25/0662* (2013.01)

(56) References Cited

U.S. PATENT DOCUMENTS

| | | | |
|---|---|---|---|
| 4,770,185 A * | 9/1988 | Silverstein | A61B 1/00177 600/454 |
| 5,053,002 A * | 10/1991 | Barlow | A61B 1/00135 604/245 |
| 5,313,934 A | 5/1994 | Wiita et al. | |
| 5,320,602 A * | 6/1994 | Karpiel | A61M 25/0668 600/101 |
| 5,419,314 A * | 5/1995 | Christopher | A61M 16/0475 128/207.29 |
| 5,630,795 A * | 5/1997 | Kuramoto | A61B 1/00137 604/35 |
| 5,842,971 A | 12/1998 | Yoon | |
| 6,695,773 B1 | 2/2004 | Dahlinger | |
| 8,096,944 B2 | 1/2012 | Harrel | |
| 8,517,927 B2 | 8/2013 | Asada et al. | |
| 8,690,831 B2 | 4/2014 | Duke | |
| 8,900,132 B2 | 12/2014 | Ishigami et al. | |
| 10,058,236 B2 * | 8/2018 | Boutillette | A61B 1/04 |
| 2004/0030220 A1 * | 2/2004 | Hamm | A61B 1/015 600/156 |
| 2005/0261553 A1 * | 11/2005 | Swain | A61M 1/777 600/156 |
| 2006/0258955 A1 * | 11/2006 | Hoffman | A61B 10/06 600/564 |
| 2007/0100235 A1 * | 5/2007 | Kennedy | A61M 25/0136 600/152 |
| 2007/0203396 A1 * | 8/2007 | McCutcheon | A61B 1/2676 600/173 |
| 2008/0114203 A1 * | 5/2008 | Crank | A61B 1/018 604/517 |
| 2011/0130632 A1 * | 6/2011 | McGrail | A61B 1/00016 600/188 |
| 2011/0130745 A1 | 6/2011 | Shevgoor et al. | |
| 2012/0022502 A1 * | 1/2012 | Adams | A61M 39/10 29/458 |
| 2012/0123209 A1 | 5/2012 | Shibuya | |
| 2013/0046145 A1 | 2/2013 | Shibuya et al. | |
| 2013/0267845 A1 * | 10/2013 | Howle | A61M 5/007 600/432 |
| 2015/0051583 A1 * | 2/2015 | Horvath | A61M 5/14248 604/523 |
| 2015/0282695 A1 | 10/2015 | Tay et al. | |
| 2016/0166807 A1 * | 6/2016 | De Stefano | A61M 25/0606 604/164.08 |
| 2016/0354140 A1 * | 12/2016 | Sharma | A61B 90/39 |
| 2017/0042528 A1 | 2/2017 | Ellegala | |
| 2017/0307872 A1 | 10/2017 | Hatase et al. | |

OTHER PUBLICATIONS

Anderson, Sterling J., et al., "Design of an Endoscope Lens Shielding Device for Use in Laparoscopic Procedures," Proceedings of the 2010 Design of Medical Devices Conference, Apr. 13-15, 2010, 8 pages.

"FloShield | Superior Laparoscopic Vision," Minimally Invasive Devices, Inc., 2019, available at http://floshield.com/, 7 pages.

* cited by examiner

DEVICE FOR SHIELDING ENDOSCOPIC OPTICS WITH A FLUID BARRIER

CROSS-REFERENCE TO RELATED APPLICATIONS

This application is a non-provisional application which claims priority to U.S. provisional application Ser. No. 62/700,007, filed Jul. 18, 2018, which is incorporated by reference herein in its entirety.

BACKGROUND

The present embodiments relate generally to medical devices, and more particularly, to systems and methods for delivering therapeutic agents to a target site while maintaining suitable visibility of the target site and surrounding environment.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of normal, healthy tissues to the therapeutic agents, which may reduce potentially harmful side effects.

Localized delivery of therapeutic agents has been performed using catheters and similar introducer devices. By way of example, a catheter may be advanced to a target site within the patient, where the therapeutic agent may be sprayed or ejected from the catheter into the target site. Typically, a syringe or similar device may be used to spray or eject the therapeutic agent from the catheter into the target site. However, such a delivery technique may result in an interrupted or unclear image or view of the target site using the imaging device of the endoscope to which the catheter is operatively coupled.

SUMMARY

The present embodiments provide systems and methods suitable for delivering a therapeutic agent to a target site while maintaining suitable visibility of the target site and surrounding environment.

In one aspect, a system suitable for delivering an agent including a plurality of particles to a target site includes a catheter having a first wall defining a lumen sized for delivery of the agent to the target site. The catheter has a distal end terminating with a primary opening of the lumen, an opposing proximal end, and a longitudinal axis extending between the distal end and the proximal end. A secondary opening is formed at the distal end, wherein the secondary opening is configured to allow fluid, e.g., gas or liquid, to flow through the secondary opening to create a steady flow of fluid at an angle with respect to the longitudinal axis and prevent the plurality of particles from flowing through the secondary opening.

In another aspect, a system suitable for delivering an agent to a target site, includes an endoscope having a proximal end and a distal end opposite the proximal end. The endoscope includes an imaging device extending through at least a portion of the endoscope between the proximal end and the distal end. The imaging device includes a lens positioned at a surface of the distal end of the endoscope. An accessory channel extends through at least a portion of the endoscope between the proximal end and the distal end. The accessory channel terminates at the surface of the distal end of the endoscope and forms a first opening at the surface of the distal end of the endoscope. A catheter is movably positioned within the accessory channel. The catheter has a first wall defining a lumen sized for delivery of the agent to the target site. The catheter has a distal end terminating with a primary opening of the lumen, an opposing proximal end, and a longitudinal axis extending between the distal end and the proximal end. In certain example embodiments, secondary opening is formed at the distal end of the catheter, wherein the secondary opening has a largest dimension less than an average diameter of particles of the agent such that fluid, e.g., gas or liquid, is allowed to flow through the secondary opening to create a steady flow of fluid at an angle with respect to the longitudinal axis and the particles are prevented from flowing through the secondary opening.

In yet another aspect, a system includes a catheter having a lumen sized for delivery of a plurality of particles to a target site. The catheter has a distal end, an opposing proximal end, and a longitudinal axis extending between the distal end and the proximal end. A plurality of secondary openings are formed through a wall of the catheter at the distal end. In example embodiments, each secondary opening has a diameter less than an average diameter of the plurality of particles such that fluid, e.g., gas or liquid, is allowed to flow through the secondary openings to create a steady flow of fluid at an angle with respect to the longitudinal axis and the plurality of particles are prevented from flowing through the secondary openings. In example embodiments, the system also includes an endoscope having a proximal end and a distal end opposite the proximal end. The endoscope includes an imaging device extending through at least a portion of the endoscope between the proximal end and the distal end. The imaging device includes a lens positioned at a surface of the distal end of the endoscope. An accessory channel extends through the endoscope between the proximal end and the distal end. The accessory channel terminates at the surface of the distal end of the endoscope, wherein the catheter is movable within the accessory channel in a distal direction and an opposing proximal direction. With the catheter in an extended position, the catheter extends distally from the surface such that the secondary openings are external to the accessory channel. In a particular embodiment, one or more indicator marks at the distal end of the catheter indicate to the user that the catheter is extended distally a distance from the surface, wherein with the catheter in the extended position, the fluid flow through the plurality of secondary openings forms a fluid curtain to prevent accumulation of debris near the lens.

Other systems, methods, features and advantages of the described embodiments will be, or will become, apparent to one with skill in the art upon examination of the following figures and detailed description. It is intended that all such additional systems, methods, features and advantages be within the scope of the disclosure, and be encompassed by the following claims.

BRIEF DESCRIPTION OF THE DRAWINGS

The embodiments can be better understood with reference to the following drawings and description. The components

DETAILED DESCRIPTION

In the present application, the term "proximal" refers to a direction that is generally towards a physician during a medical procedure, while the term "distal" refers to a direction that is generally towards a target site within a patient's anatomy during a medical procedure. As used herein to describe example embodiments, the term "fluid" may refer to a gas or a liquid. The terms "suitable for" and "configured for" are not merely statements of intention, but rather denote being constructed and dimensioned, with concrete structural limitations that will be understood by those of skill in the art with reference to the present disclosure.

In example embodiments as described herein, a system, such as an endoscope system, suitable for delivering an agent, such as a therapeutic agent, to a target site within a patient's anatomy. The system includes an endoscope having a proximal end and a distal end opposite the proximal end. The endoscope includes an imaging device extending through at least a portion of the endoscope between the proximal end and the distal end. The imaging device includes a lens positioned at a surface of the distal end of the endoscope. The lens is operatively coupled, such as in signal communication, to an external imaging system which receives one or more signals transmitted by the lens indicative of images captured by the lens of the target site and surrounding environment. The external imaging system includes one or more processors for processing the received signals and displaying on a display one or more images of the target site captured by the lens.

An accessory channel extends through at least a portion of the endoscope between the proximal end and the distal end. The accessory channel terminates at the surface of the distal end of the endoscope to form an opening at the surface of the distal end of the endoscope. In example embodiments, a catheter is movably positioned within the accessory channel. The catheter has a wall defining a lumen sized for delivery of the agent to the target site. The catheter has a distal end terminating with a primary opening, e.g., an outlet, of the lumen, an opposing proximal end terminating with an inlet opening and a longitudinal axis extending between the distal end and the proximal end. One or more secondary openings are formed at the distal end of the catheter and, in certain example embodiments, has suitable dimensions less than an average diameter of particles of the agent such that fluid, e.g., gas such as carbon dioxide, is allowed to flow through the secondary opening or secondary openings at the distal end of the catheter to create a steady flow of fluid at an angle with respect to the longitudinal axis and the particles are prevented from flowing through the secondary opening or secondary openings in the catheter as the particles exit the primary opening of the lumen at the distal end of the catheter. During operation, a pressurized fluid, e.g., a gas such as carbon dioxide, is advanced through the catheter to carry the agent particles to the target site. With the catheter in an extended position, i.e., extended distally from the accessory channel, the agent particles exit the lumen through the primary opening while at least a portion of the fluid exits the catheter, e.g., through the lumen or a coaxially positioned second lumen, through the secondary openings to create a steady fluid flow forming a fluid curtain over or near the lens to prevent or limit agent particles from obscuring or interrupting an image or view of the target site through the imaging device of the endoscope. In addition or alternatively, the fluid curtain may also be used to protect other structures, such as anatomical structures or devices, other than or in addition to the image device. As used herein to describe example embodiments, the term "fluid" may refer to a gas or a liquid.

In certain example embodiments, the catheter is movable within the accessory channel in a distal direction and an opposing proximal direction. With the catheter in an extended position, the catheter extends distally from the surface at the distal end of the endoscope such that the primary opening or primary openings are external to the accessory channel. One or more indicator marks may be located at the distal end of the catheter that are visible with the catheter in an extended position to indicate to the user that the catheter is extended distally a distance from the surface at the distal end of the endoscope. With the catheter in the extended position, the agent particles exit the lumen through the primary opening or primary openings while at least a portion of the fluid exits through secondary openings in the lumen to create a steady fluid flow forming a fluid curtain over or near the lens to prevent or limit particles from obscuring or interrupting an image or view of the target site through the imaging device of the endoscope. In addition or alternatively, the fluid curtain may also be used to protect other structures, such as anatomical structures or devices, other than or in addition to the image device.

In certain alternative example embodiments, the system includes a positive stop at the distal end of the catheter. A second wall is positioned about the first wall of the catheter, e.g., coaxially with the first wall about the longitudinal axis, to define a second lumen between the first wall and the second wall. In this embodiment, the opening at the distal end of the catheter is a continuous annular slit defined between the positive stop and a distal end of the second wall. In an alternative embodiment, the opening at the distal end of the catheter is a continuous annular slit or a plurality of discontinuous annular slit sections defined between the positive stop and the distal end of the second wall.

Figure 1:
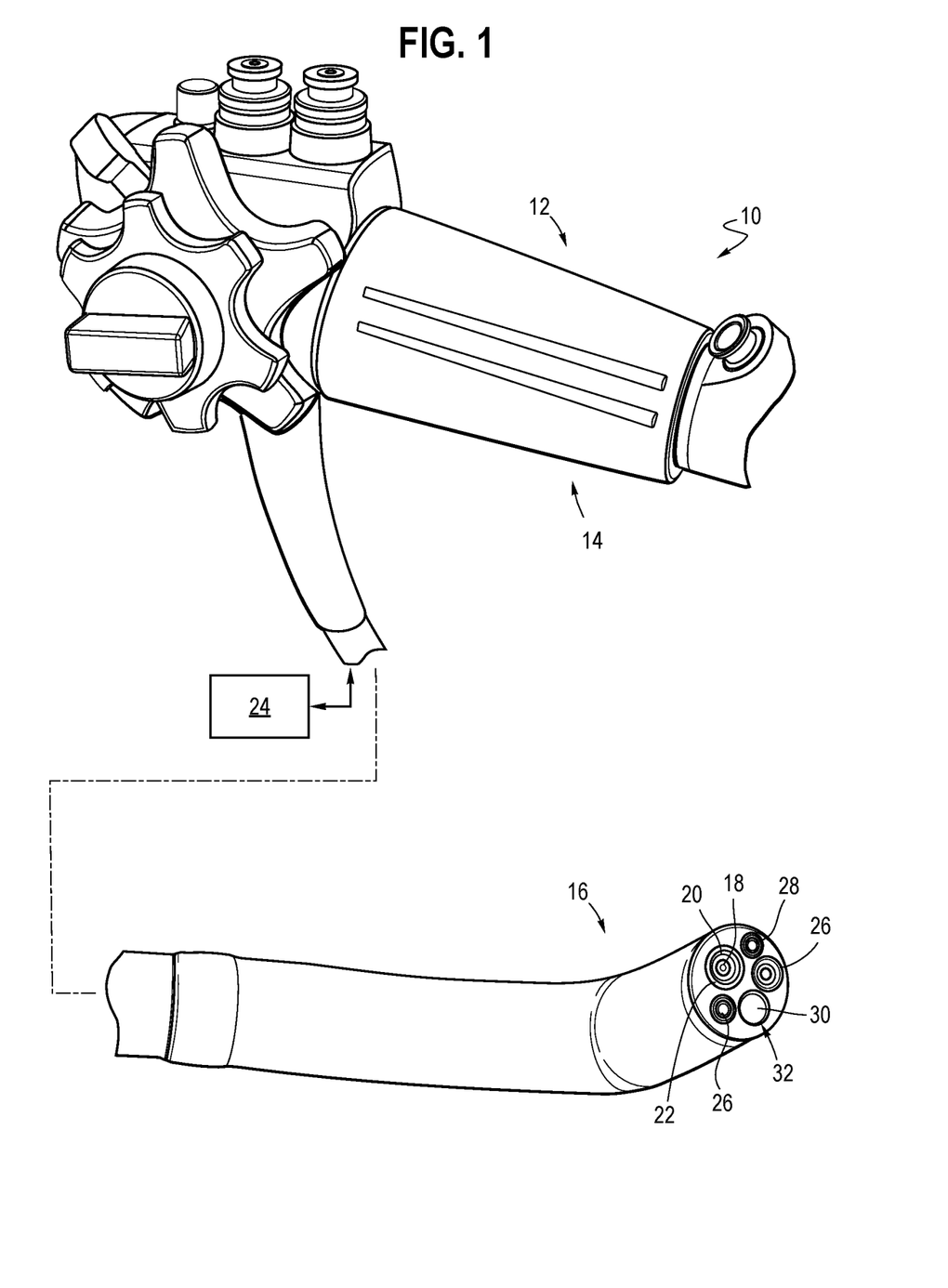
FIG. 1 is a perspective view of an example endoscope system according to certain embodiments.

Referring now to FIGS. 1-6, in example embodiments, a system 10, such as an endoscope system, suitable for delivering an agent to a target site within a patient's anatomy includes an endoscope 12, shown in FIG. 1. Generally, endoscope 12 has a proximal end 14 and a distal end 16 opposite proximal end 14. An imaging device 18 extends through at least a portion of endoscope 12 between proximal end 14 and distal end 16. Imaging device 18 including a lens 20 positioned at a surface 22 of distal end 16. Lens 20 is operatively coupled to, e.g., in signal communication with, an external imaging system 24 and is configured to capture images of the target site and transmit signals indicative of the captured images to imaging system 24. As shown in FIG. 1, for example, endoscope 12 also includes one or more light sources 26, such as light-emitting diodes (LEDs), and a water source 28 configured to inject water into the target site.

Figure 2:
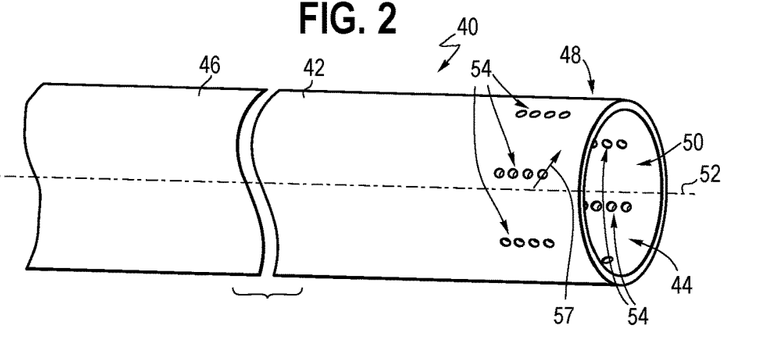
FIG. 2 is a schematic perspective view of a portion of an example catheter suitable for use with the endoscope system of FIG. 1 according to certain embodiments.

In example embodiments, endoscope 12 includes an accessory channel 30 extending through at least a portion of endoscope 12 between proximal end 14 and distal end 16. Accessory channel 30 terminates at surface 22 at distal end 16 forming an opening 32 at surface 22. Referring further to FIG. 2, system 10 also includes a catheter 40 that is movably positioned within accessory channel 30. Catheter 40 may include one or more suitable tube members for delivering the agent to a target site. For example, catheter 40 may comprise a flexible, tubular member that may be formed from one or more semi-rigid polymers including, without limitation, polyurethane, polyethylene, tetrafluoroethylene, polytetrafluoroethylene, fluorinated ethylene propylene, nylon, PEBAX or the like.

In operation, a distal end of catheter 40 may be positioned in relatively close proximity to the target site. Catheter may be advanced to the target site using a flexible endoscopic technique, an open technique, a laparoscopic technique, an intraluminal technique, using a gastroenterology technique through the mouth, colon, or using any other suitable technique. Catheter 40 may comprise one or more markers configured to be visualized under fluoroscopy or other imaging techniques to facilitate location of the distal end of catheter 40. As described herein, catheter 40 may be advanced through a working lumen, e.g., an accessory channel 30, of an endoscope 12. When the catheter 40 is positioned at the desired target site, the pressure source to urge the pressurized fluid to flow through catheter 40, thereby delivering the agent to the target site at a desired pressure.

Figure 3:
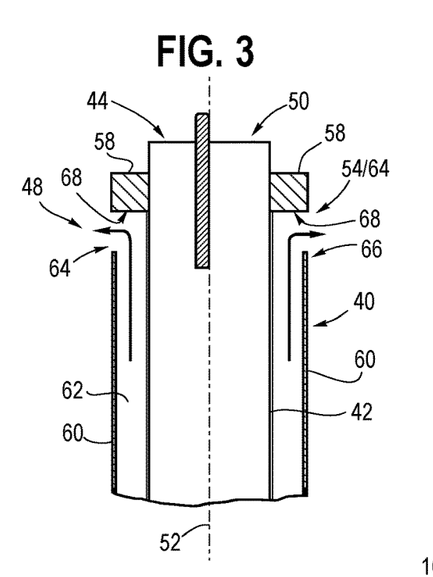
FIG. 3 is a schematic view of a portion of an alternative example catheter suitable for use with the endoscope system of FIG. 1 according to certain embodiments.

Catheter 40 includes a wall 42 defining a lumen 44 sized for delivery of the agent, such as a therapeutic agent, to the target site. Catheter 40 has a proximal end 46 and an opposing distal end 48 terminating with a primary opening 50 into lumen 44. A longitudinal axis 52 extends between proximal end 46 and distal end 48 of catheter 40. Catheter 40 includes one or more secondary openings 54 formed at distal end 48. For example, in certain embodiments, at least one secondary opening 54 is formed through wall 42, e.g., a plurality of secondary openings 54 are formed through wall 42, as shown in FIG. 2, or, in alternative example embodiments, at least one secondary opening 54 is formed as an annular slit 64 at distal end 48 of catheter 40, as shown in FIG. 3.

Secondary opening 54 may have any suitable shape and/or configuration including, without limitation, an orifice, a slit, and/or an aperture formed at distal end 48 of catheter 40. Each secondary opening 54 is configured to have an area or dimensions, e.g., a diameter and/or a largest dimension, less than an average diameter of the agent particles such that fluid, e.g., gas such as carbon dioxide or a liquid, is allowed to flow through each secondary opening 54 to create a steady flow of fluid at an angle with respect to longitudinal axis 52 while the particles are prevented from flowing through secondary opening 54 but rather exit catheter 40 through primary opening 50 of lumen 44. Any suitable pressurized gas including, for example, carbon dioxide or nitrogen, compatible with the human body may be used to move the agent particles through catheter 40. In example embodiments, an axis 57 of at least one secondary opening 54 is positioned at an angle with respect to longitudinal axis 52 of 30° to 150°. In certain example embodiments, secondary opening 54 is positioned such that the fluid, e.g., gas, flows tangential to longitudinal axis 52. In certain embodiments, axis 57 of secondary opening 54 is positioned at an angle with respect to longitudinal axis 52 of less than 90° in the proximal direction to allow the diameter of secondary opening 54 to be greater than an average diameter of agent particles.

Figure 4:
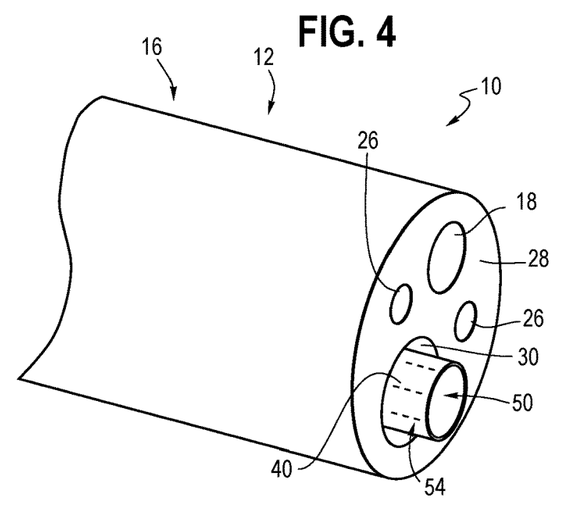
FIG. 4 is a perspective view of a portion of the endoscope system with the catheter in a distally extended position.

As shown, for example, in FIG. 4, catheter 40 is movable within accessory channel 30 in a distal direction along longitudinal axis 52 and an opposite proximal direction along longitudinal axis 52. With catheter 40 in an extended position shown in FIG. 4, catheter 40 extends distally from surface 22 such that each secondary opening 54 is external to accessory channel 30. Catheter 40 may include one or more indicator marks at distal end 48 to indicate to the user that catheter 40 is extended distally a distance from surface 22 at distal end 16 of endoscope 12. With catheter 40 in the extended position, the fluid flow through the secondary openings 54 forms a fluid curtain over or near lens 20 to prevent or limit accumulation of debris on or near lens 20, to maintain suitable visibility of the target site through lens 20.

Referring to FIGS. 2 and 4, in example embodiments, a plurality of secondary openings 54 are formed through wall 42 of catheter 40 at distal end 48. Each secondary opening 54 in these embodiments has a diameter of 50 micrometers to 200 micrometers and, in particular embodiments, each secondary opening 54 has a diameter of less than 100 micrometers. As described above, in certain example embodiments, axis 57 of one or more secondary openings 54 is positioned at an angle with respect to longitudinal axis 52 of less than 90° in the proximal direction to allow the diameter of secondary opening 54 to be greater than an average diameter of agent particles. Further, each secondary opening 54 is positioned not greater than 10.0 centimeters (cm) from distal end 48 of catheter 40, and, in particular embodiments, each secondary opening 54 is positioned not greater than 2.0 cm from distal end 48 of catheter 40. Openings may be formed symmetrically about an outer circumference of wall 42 and/or may be arranged in rows spaced circumferentially from adjacent rows. For example, secondary openings 54 may be formed in six (6) rows spaced circumferentially about an outer surface of wall 42 at an angle of 60° from adjacent rows of secondary openings 54. Alternatively, secondary openings 54 may be formed in eight (8) rows spaced circumferentially about the outer surface of wall 42 at an angle of 45° from adjacent rows of secondary openings 54.

Referring now to FIG. 3, in an alternative example embodiment, catheter 40 includes a positive stop 58 at distal end 48. A second wall 60 is positioned about wall 42 to define a second lumen 62 between wall 42 and second wall 60. In a particular embodiment, second wall 60 is positioned coaxially with wall 42 about longitudinal axis 52 of catheter 40. In this embodiment, such as shown in FIG. 3, secondary opening 54 is a continuous annular slit 64 defined between a distal end 66 of second wall 60 and a proximal surface 68 of positive stop 58. In certain example embodiments, with catheter 40 in an extend position, continuous annular slit 64 is positioned not greater than 10.0 cm from distal end 48 of catheter 40 and, in particular embodiments, continuous annular slit 64 is positioned not greater than 2.0 cm from distal end 48 of catheter 40. In a particular embodiment, an axis of continuous annular slit 64 is positioned at an angle with respect to longitudinal axis 52 of 30 degrees to 150 degrees.

In alternative embodiments, secondary opening 54 may include a plurality of discontinuous slit sections positioned about the circumference of second wall 60 and/or positive stop 58 to form a discontinuous annular slit (not shown in FIG. 3). In further alternative embodiments, second wall 60 is positioned about, e.g., positioned coaxially with, wall 42 to define second lumen 62 between wall 42 and second wall 60 and secondary opening 54, e.g., continuous annular slit 64, is formed through second wall 60.

In one embodiment, the catheter is suitable for delivering an agent, such as a therapeutic agent, to a target site. The catheter has a lumen sized for delivery of the agent to the target site. The catheter has a distal end, an opposing proximal end, and a longitudinal axis extending between the distal end and the proximal end. A plurality of secondary openings are formed through a wall of the catheter at the distal end. Each secondary opening of the plurality of secondary openings has a diameter less than an average diameter of agent particles such that fluid, e.g., gas, is allowed to flow through the plurality of secondary openings to create a steady flow of fluid at an angle with respect to the longitudinal axis, e.g., tangential to the distal end of the catheter and the particles are prevented from flowing through the plurality of secondary openings. The system includes an endoscope having a proximal end and a distal end opposite the proximal end. The endoscope includes an imaging device that extends through at least a portion of the endoscope between the proximal end and the distal end. The imaging device includes a lens positioned at a surface of the distal end of the endoscope. An accessory channel extends through at least a portion of the endoscope between the proximal end and the distal end of the endoscope. The accessory channel terminates at the surface of the distal end of the endoscope to form an opening at the surface of the distal end of the endoscope. The catheter is movable within the accessory channel in a distal direction and an opposing proximal direction. With the catheter in an extended position, the catheter extends distally from the surface of the distal end of the endoscope such that the secondary openings are external to the accessory channel. In a particular embodiment, an indicator mark at the distal end of the catheter indicates to the user that the catheter is extended distally a distance from the surface of the distal end. With the catheter in the extended position, the fluid flow through the secondary openings forms a fluid curtain over or near lens to prevent or limit accumulation of debris on or near lens and maintain suitable visibility of the target site through lens.

Figure 5:
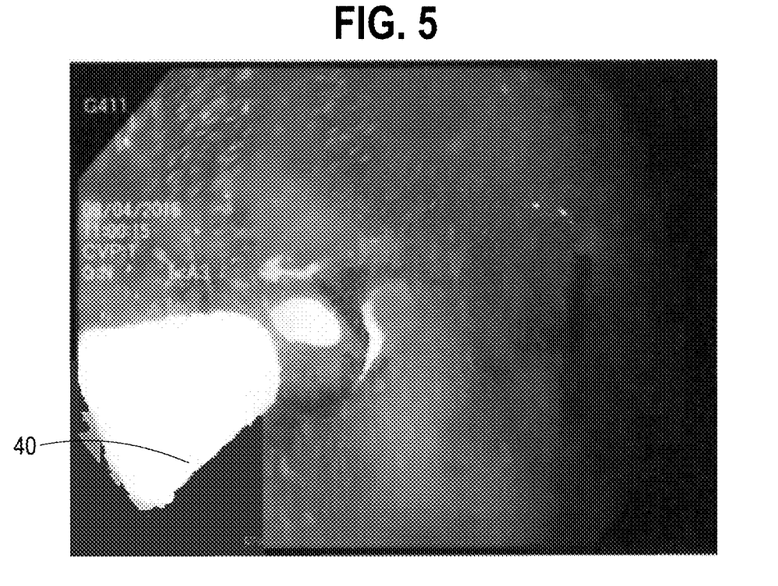
FIG. 5 is an image of a target site in which the catheter is in the extended position, and fluid flow through the secondary openings forms a fluid curtain over or near lens to prevent or limit accumulation of debris on or near lens and maintain suitable visibility of the target site through lens.
Figure 6:
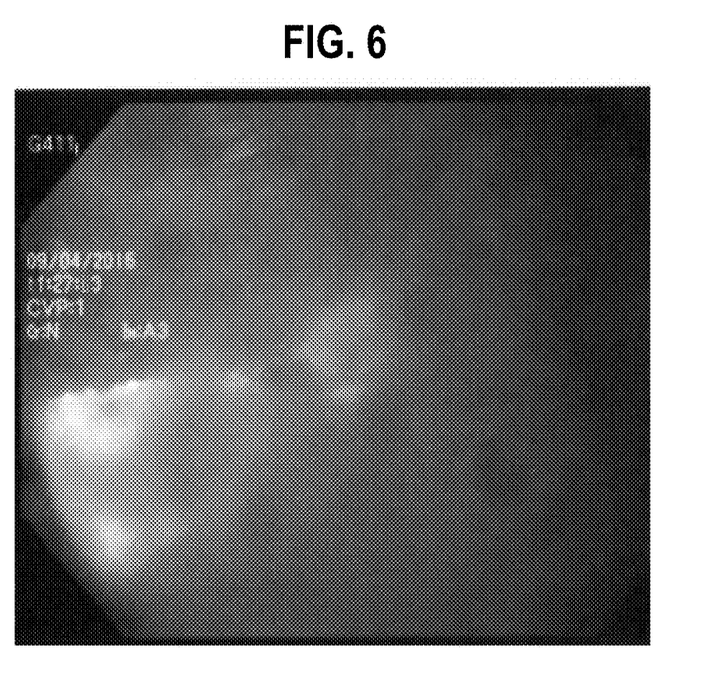
FIG. 6 is an image of the target site shown in FIG. 5 without the catheter providing the fluid curtain.

FIG. 5 is an image of a target site in which catheter 40 is in an extended position and provides the fluid flow through secondary openings 54 to form a fluid curtain over or near lens 20 to prevent or limit accumulation of debris on or near lens 20 and maintain suitable visibility of the target site through lens 20. Conversely, FIG. 6 is an image of the target site shown in FIG. 5 without catheter 40 in the extend position and providing the fluid flow forming the fluid curtain over or near lens 20.

System 10 may be used to deliver the agent in a wide range of procedures and the agent, e.g., a therapeutic agent, may be chosen to perform a desired function upon ejection from distal end 48 of catheter 40. For example, the provision of the therapeutic agent may be used for providing hemostasis, closing perforations, performing lithotripsy, treating tumors and cancers, treat renal dialysis fistulae stenosis, or vascular graft stenosis. The agent can be delivered during procedures such as coronary artery angioplasty, renal artery angioplasty and carotid artery surgery, or may be used generally for treating various other cardiovascular, respiratory, gastroenterology or other conditions. The above-mentioned systems also may be used in transvaginal, umbilical, nasal, and bronchial/lung related applications.

For example, if used for purposes of hemostasis, thrombin, epinephrine, or a sclerosant may be provided to reduce localized bleeding. Similarly, if used for closing a perforation, a fibrin sealant may be delivered to a localized lesion. In addition to the hemostatic properties of the agent, it should be noted that the relatively high pressure of the fluid and the agent, by itself, may act as a mechanical tamponade by providing a compressive force, thereby reducing the time needed to achieve hemostasis.

The agent may be selected to perform one or more desired biological functions, for example, promoting the ingrowth of tissue from the interior wall of a body vessel, or alternatively, to mitigate or prevent undesired conditions in the vessel wall, such as restenosis. Many other types of agents may be used in conjunction with system 10.

The agent may be delivered in any suitable form. For example, the agent may comprise a powder, liquid, gel, aerosol, other substances or combinations thereof. Advantageously, the pressure source may facilitate delivery of the agent in any one of these forms. The agent employed also may include an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the agent may include thrombolytic agents used to dissolve blood clots that may adversely affect blood flow in body vessels. A thrombolytic agent is any therapeutic agent that either digests fibrin fibers directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA. The therapeutic agent 38 may comprise coating-forming agents to protect or assist in healing of lesions and/or wounds. While a few exemplary agents have been described, it will be apparent that numerous other suitable agents, e.g., therapeutic agents, may be used in conjunction with system 10 and delivered through catheter 40.

Advantageously, system 10 permits localized delivery of a desired quantity of the agent at a desired, regulated pressure. Since distal end 48 of catheter 40 may be placed in relatively close proximity to a target site, system 10 provides significant advantages over agents delivered orally or through an IV system and may reduce accumulation of the agent in healthy tissues, thereby reducing side effects. Moreover, the delivery of the agent to the target site is performed in a relatively fast manner due to the relatively high pressure of the fluid, thereby providing a prompt delivery to the target site compared to previous devices.

Further, if an optional needle is employed at distal end 48 of catheter 40, system 10 advantageously may be used to both perforate tissue at or near a target site, then deliver the agent at a desired pressure in the manner described above. For example, the needle may comprise an endoscopic ultrasound (EUS) needle. Accordingly, in one exemplary technique, a sharpened tip of the needle may be capable of puncturing through an organ or a gastrointestinal wall or tissue, so that the agent may be delivered at a predetermined pressure in various bodily locations that may be otherwise difficult to access. One or more delivery vehicles, such as an endoscope or sheath, may be employed to deliver catheter 40 to a target site, particularly if distal end 48 of catheter 40 includes the optional needle.

In example embodiments, the agent has a specific range of properties that make it suitable for delivery through catheter 40, particularly when catheter 40 is sized for delivery through a lumen of an endoscope. In particular, the mass of an individual particle of the agent should be within a specific range. If a particle of the agent is too heavy, it will require too much pressure to travel the length of catheter 40 and may result in clogging of catheter 40. If the particle is too light, it will aerosolize within the patient's body, e.g., in the gastrointestinal space, instead of being propelled to a target site. In addition to mass of an individual particle of the agent, the size of the particle is important for ensuring proper delivery through catheter 40. If the agent particle is too large in size, then it will be prone to clogging within catheter 40. If the particle is too small, it may have a higher likelihood of being aerosolized instead of being propelled to the target site and/or it may undesirably exit the lumen through a secondary opening.

In example embodiments, the particles of the agent have a diameter less than 200 micrometers. Further, in example embodiments, the particles of the agent have a mass in the range of about 0.0001 milligram (mg) to about 0.5 mg, and, more particularly, the particles of the agent have a mass in the range of about 0.0001 mg to about 0.25 mg. It has been determined through multiple testing exercises that such ranges have criticality in terms of significantly reducing the likelihood of clogging of catheter 40 during delivery, and also significantly reducing the likelihood of having the particles aerosolize during delivery, and therefore be properly delivered to a target site in the correct dose.

Particles of the agent may be ground, compacted and/or sieved to produce the desired particle size and mass. As used herein, particle mass is dependent on the density of the material and the volume of the particle. Further, regarding size, an assumption can be made that the particles are spheres, in which case the diameter ranges noted herein apply. However, it will be appreciated that other particle shapes exist, especially for crystalline materials. If the particle is substantially non-spherical, then similar micrometer ranges listed herein for spherical particles may apply, but instead of referring to diameter the value may refer to average or largest dimension of the particle.

With regard to dimensions of catheter 40, when used in endoscopic applications, it is clinically important to size catheter 40 to be small enough to fit through a working lumen of the endoscope, e.g., the accessory channel, yet be large enough to substantially avoid clogging when the agent is advanced through catheter 40. In one embodiment, a ratio of catheter inner diameter to particle size diameter is at least 4:1, and, more particularly, at least 7.5:1.

It should be noted that endoscopes are generally available with accessory channels up to 4.2 millimeters (mm). Because a catheter inserted through the accessory channel has a wall thickness of generally greater than 0.25 mm, the maximum projected inner diameter of the catheter for endoscopic delivery would be 3.7 mm. Based on a 4:1 ratio of catheter inner diameter to particle diameter, then the maximum acceptable particle diameter would be approximately 925 microns. Further, it is noted that spherical particles may be less susceptible to clogging than cuboid or flat particles. Accordingly, a ratio of closer to 4:1 may be acceptable for spherical particles, whereas a higher ratio (e.g., 7.5:1 or greater) may be acceptable for other particle shapes.

With regard to pressure, as noted above, the pressure source may include a pressurized fluid cartridge of a selected gas or liquid, such as carbon dioxide, nitrogen, or any other suitable gas or liquid that may be compatible with the human body. The pressurized fluid cartridge may contain the gas or liquid at a relatively high, first predetermined pressure, for example, around 1,800 pounds per square inch (psi) inside of the cartridge. The pressure source may be in a solid (dry ice), liquid or gas state. As further noted above, the fluid may flow from the pressure source through a pressure regulator, such as a regulator valve having a pressure outlet, which may reduce the pressure to a lower, second predetermined pressure (referred to here as a "delivery system pressure"). In one embodiment, it has been found beneficial to have a delivery system pressure in the range of 0.01 psi to 100 psi, and, more particularly, in the range of about 0.5 psi to about 75 psi. Such ranges may have criticality in terms of providing appropriate force to propel the agent through catheter 40, while significantly reducing the likelihood of clogging of catheter 40 during delivery, and therefore properly deliver the agent to a target site in the correct dose. It should be noted that the inventor has also demonstrated delivery using a syringe filled with a powder and air that is manually compressed.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more examples of implementations.

It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments. In general, of course, these and other issues can vary with the particular context of usage. Therefore, the particular context of the description or the usage of these terms can provide helpful guidance regarding inferences to be drawn for that context.

What is claimed is:

1. A system suitable for delivering an agent including a plurality of particles to a target site, the system comprising:
   the agent including the plurality of particles; and
   an endoscope having a proximal end and a distal end opposite the proximal end, the endoscope comprising:
      an imaging device extending through at least a portion of the endoscope between the proximal end and the distal end, the imaging device including a lens positioned at a surface of the distal end of the endoscope; and
      an accessory channel extending through at least a portion of the endoscope between the proximal end and the distal end, the accessory channel terminating at the surface of the distal end of the endoscope and forming a first opening at the surface of the distal end of the endoscope; and
   a catheter movably positioned within the accessory channel, the catheter having a first wall defining a lumen sized for delivery of the agent to the target site, the catheter having a distal end terminating with a primary opening of the lumen, an opposing proximal end, and a longitudinal axis extending between the distal end and the proximal end, and a secondary opening formed at the distal end of the catheter, wherein the secondary opening has a largest dimension different than an average diameter of the plurality of particles of the agent such that fluid is allowed to flow through the secondary opening to create a steady flow of fluid at an angle with respect to the longitudinal axis and the plurality of particles is prevented from flowing through the secondary opening.

2. The system of claim 1, wherein the catheter is movable within the accessory channel in a distal direction and an opposing proximal direction, and with the catheter in an extended position, the catheter extends distally from the surface such that the secondary opening is external to the accessory channel.

3. The system of claim 1, further comprising an indicator mark at the distal end of the catheter to indicate to the user that the catheter is extended distally a distance from the surface, wherein with the catheter in the extended position, the fluid flow through the secondary opening forms a fluid curtain to prevent accumulation of debris near the lens.

4. The system of claim 1, wherein the secondary opening has a diameter less than 100 micrometers.

5. The system of claim 1, wherein the secondary opening is positioned not greater than 2.0 centimeters from the distal end of the catheter.

6. The system of claim 1, wherein the secondary opening is positioned not greater than 3.0 millimeters from the distal end of the catheter.

7. The system of claim 1, wherein the secondary opening is formed through the first wall at the distal end of the catheter.

8. The system of claim 7, wherein an axis of the secondary opening is positioned at an angle with respect to the longitudinal axis of 30 degrees to 150 degrees.

9. The system of claim 7, wherein an axis of the secondary opening is positioned at an angle with respect to the longitudinal axis of less than 90 degrees in a proximal direction and a diameter of the secondary opening is greater than an average diameter of the plurality of particles.

10. The system of claim 7, wherein a plurality of secondary openings is formed through the first wall of the catheter at the distal end.

11. The system of claim 10, wherein each secondary opening of the plurality of secondary openings is positioned not greater than 2.0 centimeters from the distal end of the catheter.

12. The system of claim 10, wherein each secondary opening of the plurality of secondary openings is positioned not greater than 3.0 millimeters from the distal end of the catheter.

13. The system of claim 10, wherein an axis of at least one secondary opening of the plurality of secondary openings is positioned at an angle with respect to the longitudinal axis of 30 degrees to 150 degrees.

14. The system of claim 10, wherein an axis of at least one secondary opening of the plurality of secondary openings is positioned at an angle with respect to the longitudinal axis of less than 90 degrees in a proximal direction and a diameter of the at least one secondary opening is greater than an average diameter of the plurality of particles.

15. A system suitable for delivering an agent including a plurality of particles to a target site, the system including:
   the agent including the plurality of particles; and
   a catheter having a lumen sized for delivery of the agent to the target site, the catheter having a distal end, an opposing proximal end, and a longitudinal axis extending between the distal end and the proximal end, and a plurality of secondary openings formed through a wall of the catheter at the distal end, wherein each secondary opening of the plurality of secondary openings has a diameter less than an average diameter of the plurality of particles of the agent such that fluid is allowed to flow through the plurality of secondary openings to create a steady flow of fluid at an angle with respect to the longitudinal axis and the plurality of particles is prevented from flowing through the plurality of secondary openings.

16. The system of claim 15, further comprising:
   an endoscope having a proximal end and a distal end opposite the proximal end, the endoscope comprising:
      an imaging device extending through at least a portion of the endoscope between the proximal end and the distal end, the imaging device including a lens positioned at a surface of the distal end of the endoscope; and
      an accessory channel extending through the endoscope between the proximal end and the distal end, the accessory channel terminating at the surface of the distal end of the endoscope, wherein the catheter is movable within the accessory channel in a distal direction and an opposing proximal direction, and with the catheter in an extended position, the catheter extends distally from the surface such that the plurality of secondary openings is external to the accessory channel.

17. The system of claim 16, further comprising an indicator mark at the distal end of the catheter to indicate to the user that the catheter is extended distally a distance from the surface, wherein with the catheter in the extended position, the fluid flow through the plurality of secondary openings forms a fluid curtain to prevent accumulation of debris near the lens.

\* \* \* \* \*